United States Patent [19]

Gabriel et al.

[11] Patent Number: 5,120,893

[45] Date of Patent: Jun. 9, 1992

[54] PROCESS FOR CATALYTICALLY CONVERTING C10 AND HIGHER OLEFINS TO C9 AND LOWER OLEFINS

[75] Inventors: Joseph W. Gabriel, Clearwater; Alexandr P. Glivicky, Sarnia; Nur R. Gurak; Norman C. Murtaugh, both of Clearwater, all of Canada; Wilfried J. Mortier, Hellevoetsluis, Netherlands; David E. Vaughan, Flemington, N.J.; Ram N. Bhatia, Baton Rouge, La.

[73] Assignee: Exxon Chemical Patents Inc., Linden, N.J.

[21] Appl. No.: 580,659

[22] Filed: Sep. 11, 1990

[51] Int. Cl.$^5$ .................. C07C 4/02; C10G 11/03
[52] U.S. Cl. ................... 585/653; 585/648; 208/120; 208/119; 208/118
[58] Field of Search ............. 585/653, 648; 208/120, 208/119, 118

[56] References Cited

U.S. PATENT DOCUMENTS

| | | | |
|---|---|---|---|
| 3,140,249 | 7/1964 | Plank et al. | 208/120 |
| 3,308,609 | 3/1967 | McCulloch et al. | 55/319 |
| 3,702,886 | 11/1972 | Argauer et al. | 423/328 |
| 3,709,979 | 1/1973 | Chu | 423/328 |
| 4,061,724 | 12/1977 | Grose et al. | 423/335 |
| 4,429,424 | 2/1984 | Waldner | 4/479 |

FOREIGN PATENT DOCUMENTS 0109059 5/1984 European Pat. Off. .
0109060 5/1984 European Pat. Off. .

OTHER PUBLICATIONS

The Canadian Journal of Chem. Eng., vol. 63, Jun. 1985, "The Mechanism of Catalytic Cracking of n-Alkenes on ZSM-5 Zeolite", J. Abbot and B. W. Wojciechowski, pp. 462-469.

*Primary Examiner*—Anthony McFarlane
*Assistant Examiner*—Nhat Phan

[57] ABSTRACT

The present invention provides a highly selective catalytic cracking process for the conversion of feedstocks containing a predominant content of $C_{10}$ and higher mixed olefins into $C_9$ and lower olefin products at efficiencies of greater than 20%. said products further characterized in that the content $C_6$ to $C_9$ olefins is maximized while the content of $C_2$ to $C_4$ olefins is minimized. The process involves contacting an olefin feedstock mixture containing at least about 50 weight %, more preferably at least about 70 weight %, of $C_{10}$ and higher olefins under cracking conditions with a catalyst selected from the group consisting of amorphous precipitated silica, selected crystalline silicates and aluminosilicates, namely beta, mordenite and ZSM-5 types, as well as ion exchanged or acid variants thereof. Cracking conditions include a temperature within the range of from about 250° up to about 450° C., pressures from atmospheric up to about 300 psig and a space velocity within the range of from about 0.5 up to about 4 wt/wt/hour.

18 Claims, No Drawings

PROCESS FOR CATALYTICALLY CONVERTING C10 AND HIGHER OLEFINS TO C9 AND LOWER OLEFINS

BACKGROUND OF THE INVENTION

1. Field of the Invention

The present invention relates to a catalytic cracking process for converting $C_{10}$ and higher olefin materials into more useful $C_9$ and lower olefin materials having a high value in petrochemical and fuel applications.

2. Description of Related Art

One of the significant applications of $C_2$ to $C_4$ light olefins including propylene and butene-1, involves their conversion by pyrolysis or polymerization processes into higher olefin oligomers or to other products useful as high octane gasoline components. Incidental to such processes is the formation of minor amounts of olefin by-product materials having a predominant $C_{10}$ and $C_{11}$ olefin component with lesser $C_9$ and $C_{12}$ components, together with minor amounts of $C_{13}^+$ olefins.

These higher olefin by-product components are generally separated from the primary oligomer product and are collected for other uses. The composition of such collected by-products generally includes at least about 70 weight % of branched mixed $C_{10}$ and $C_{11}$ olefins, up to about 15 weight % of branched $C_9$ olefins and up to about 20 weight % of branched $C_{12}^+$ olefins. Since it is difficult to further separate these materials into purer higher olefins and since these olefins are not as commercially valuable as are the lower olefins such as hexene, heptene, octene and nonene, this higher olefin mixture is normally distributed as a component for mogas or bunker fuel.

Various processes are known in the art for the catalytic cracking of heavier olefins into lighter olefins. For example, European Patent Publication 0109059 discloses the conversion of $C_4$ to $C_{12}$ olefins into propylene and lesser amounts of ethylene using modified or nonmodified zeolite catalysts having a Si to Al ratio of 300 or less. Process conditions are space velocities higher than 50 kg/h, temperatures of 400°–600° C. and pressures slightly above atmospheric. The zeolite catalyst may be modified by ion exchange with compounds providing other ions such as ammonium ions. The preferred fractions to be cracked are butenes (Ex. 1–20), n-pentene-1 (Ex. 22–44) n-hexane (Ex. 45–48) and 2-methyl-1-pentene (Ex. 51 and 52).

European Patent Publication 0109060 discloses a similar process except that the zeolite catalyst is characterized as having a Si to Al ratio of greater than 350 and the catalyst may also include materials such as silicalites and their boron and chromium substituted polymorphs. Cracking conditions include space velocities of 5 to 200 kg/h, temperatures of 400° to 600° C. and pressures of slightly above atmospheric up to 8 atmospheres.

However, the processes disclosed in each of these references is highly selective towards the formation of $C_3$ and $C_4$ compounds, largely as a consequence of the composition of the feedstock and the relatively high cracking temperatures and space velocities employed in the process.

Abbot et al. in the Canadian Journal of Chemical Engineering, Vol. 63, June 1985, teaches the catalytic cracking of substantially pure n-alkenes (hexenes through nonenes) at 405° C. using a Zeolite ZSM-5 catalyst. The reference indicates that olefins smaller than $C_6$ are stable to cracking and must first dimerize before a species is formed susceptible to cracking, whereas higher olefins up to nonenes are subject to monomolecular cracking to yield mixed lower olefins, such as mixtures of two or more of $C_3$, $C_4$, $C_5$ and $C_6$ olefins. This process is selective towards the formation of $C_6$ and lower olefins largely as a function of the cracking temperatures and composition of the relatively pure olefin feedstock.

Zeolite materials have long been known in the art and have been used as cracking and petrochemical conversion catalysts, as well as molecular sieves for molecular separation. The materials and applications of Zeolites are disclosed in various publications: Barrer, "Zeolites and Clay Minerals as Sorbents and Molecular Sieves", Academic Press, London, 1978; Breck, "Molecular Sieves", (1974), J. Wiley, (New York). They may be characterized as crystalline aluminosilicates having a rigid three dimensional network of $SiO_4$ and $AlO_4$ in which the tetrahedra are crosslinked by the sharing of oxygen atoms whereby the ratio of the total aluminum and silicon atoms to oxygen is about 1:2. The electrovalence of the tetrahedra-containing aluminum is balanced by the inclusion in the crystal of a cation such as an ammonium ion, an alkali or alkaline earth metal ion or mixtures thereof, or by a hydrogen ion in the acid form.

U.S. Pat. No. 3,140,249 discloses a zeolite type catalyst which has been modified by ion exchange to replace the alkali metal ion with another ion. The catalyst is disclosed to be useful in cracking hydrocarbon oils to lighter materials boiling in the gasoline range under cracking temperatures of at least 700° F.

U.S. Pat. No. 3,702,886 discloses a zeolite catalyst designated as "ZSM-5" useful, inter alia, for cracking hydrocarbons. The catalyst may be useful in the alkali metal form or exchanged with ammonium or a different metal.

U.S. Pat. No. 3,709,979 discloses zeolite ZSM-11 which may be used for cracking hydrocarbons. The catalyst may be used in the alkali metal form or may be ion exchanged.

U.S. Pat. No. 3,308,609 teaches a method for the production of a zeolite referred to as Zeolite beta by forming the crystallization product from an aqueous reaction mixture comprising amorphous silica, a soluble aluminate and tetraethylammonium aluminate. The catalyst may be used in the alkali metal form or may be ion exchanged using a different metal.

"Silicalite" may be characterized as a near pure silica form of ZSM-5. In this context, the term silicalites also includes various intergrowth forms, alternately called "pentasils" in the literature such as disclosed in U.S. Pat. No. 4,229,424 and by Kokotailo et al., Chemical Society Special Publication #33, Ed. R. P. Townsend, p. 133 (1980).

Such materials are referred to in the aforementioned E. P. 0109060. In addition, U.S. Pat. No. 4,061,724 discloses the preparation of "silicalite" by a hydrothermal crystallization of a reaction mixture comprising water, a source of silica and an alkylammonium compound, followed by calcination. This material is a ZSM-5 type with a very high content of $SiO_2$.

These and other catalyst systems and processes are particularly useful in cracking hydrocarbon oils and in numerous petrochemical processes. While these are useful products and processes, it would be particularly desirable to develop a process for cracking $C_{10}^+$ higher olefins which demonstrates selectivity towards the production of olefins in the $C_6$ to $C_9$ product fraction boiling within the range of 20° to 154° C., and particularly a process which leads to enhanced yields of hexene, heptene, octene and nonene while minimizing the production of $C_2$ to $C_4$ olefins and saturated hydrocarbons. These $C_6$–$C_9$ olefins are particularly useful as feedstocks in the production of alcohols, alkyl phenols, acetates and like chemicals which have numerous industrial applications such as surfactants, plasticizers, resin-forming reactants and the like.

SUMMARY OF THE INVENTION

The present invention provides a highly selective catalytic cracking process for the conversion of feedstocks containing a predominant content of $C_{10}$ and higher mixed olefins into $C_9$ and lower olefin products at efficiencies of greater than 20%, said products further characterized in that the content $C_6$ to $C_9$ olefins is maximized while the content of $C_2$ to $C_4$ olefins is minimized. The process involves contacting an olefin feedstock mixture containing at least about 50 weight %, more preferably at least about 70 weight %, of $C_{10}$ and higher olefins under cracking conditions with a catalyst selected from the group consisting of modified amorphous precipitated silica, selected crystalline silicates and aluminosilicates, particularly beta, mordenite, and ZSM-5 types, and ion exchanged or acid variants thereof. Cracking conditions include a temperature within the range of from about 250° up to about 450° C., pressures from atmospheric up to about 300 psig and a space velocity within the range of from about 0.5 up to about 4 wt/wt/hour.

DETAILED DESCRIPTION OF THE INVENTION

As indicated above, the high silica-based catalysts useful for the purposes of the present invention include selected crystalline silicates and aluminosilicates, precipitated amorphous silica, and ion exchanged or acid modified forms thereof.

The category of crystalline aluminosilicates which are used in accordance with this invention may be generally categorized as zeolites of the formula:

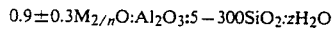
$0.9 \pm 0.3 M_{2/n}O:Al_2O_3:5-300SiO_2:zH_2O$ wherein M is a cation or mixture of cations and n is the valence or average valence of said cation(s), and Z ranges from 0 to 40. In the dehydrated form, Z is, of course, 0.

The preferred zeolites of the above formula are those where the M cations include alkali metals and alkaline earth metals, hydrogen, ammonium, and mixtures thereof. The catalysts may also be used in the modified form such as where the cation present in the zeolite (as synthesized) is partially or totally replaced using conventional ion exchange by a different cation such as ammonium, magnesium, hydrogen or a metal ion selected from Groups II to VIII of the Periodic Table, most preferably alkaline earth metal ions, rare earth metal ion, Group 2 metal ions and ions of transition metals such as manganese and nickel. The hydrogen or acid form of the zeolite may be prepared by ion exchange treatment of the alkali metal form with a strong inorganic acid such as hydrochloric acid, or by ion exchange with an ammonium compound such as ammonium chloride, ammonium nitrate, or an equivalent $NH_4^+$ source, followed by calcination to at least partially decompose the ammonium form to produce the acid form. Where the Zeolite is synthesized in a form combining a trapped template ion, calcination at temperatures of 350° to 700° C. to remove the template ion will precede the aforementioned ion exchange process.

More preferred zeolites are those having an $SiO_2$ to $Al_2O_3$ ratio of from about 3:1 to 1000:1, most preferably from about 40:1 to about 100:1, and a degree of hydration such that Z in the formula above ranges from 0 to about 5.

Preferred synthetic Zeolites for the purposes of this invention are the as synthesized or cation exchanged forms of ZSM-5, such as disclosed in U.S. Pat. Nos. 3,702,886 and 3,926,782; and beta zeolite such as disclosed in U.S. Pat. No. 3,308,069. Particularly preferred are the modified forms of ZSM-5 such as silicalite which may be produced in accordance with U.S. Pat. No. 4,061,724. Silicalite is a near pure form of silica and is isostructural with ZSM-5, or intergrowth forms thereof. These aforementioned patents are each incorporated herein by reference.

Naturally occurring crystalline zeolites having a Si to Al ratio of at least 3 to 1 and which have been ion exchanged by the techniques described above may also be used as catalysts for the purposes of this invention. Such materials include mordenite, erionite and clinoptiloile. Ion exchanged mordenite having a Si to Al ratio of from about 5 to about 15, more preferably about 10, and having a crystal size of less than about 0.5 microns is particularly preferred species.

A second category of silicon-containing catalyst which may be used in accordance with this invention is amorphous precipitated silica having a $SiO_2$ content of greater than 99% by weight, a surface area of from about 150 to 250 $M^2/g$ and a pore volume of from about 0.03 to about 1.5 cc/g. Preferably this material is employed in the activated or activated/acidified form. In contrast to the Zeolite materials, this material has no crystalline structure but comprises a random network of linked silicate tetrahedra. Activation may be accomplished by heating the material at a temperature of at least 350° C. for one or more hours prior to contact with the feedstock. The activated/acidified form of the product is achieved by ion infusion of the material with $H^+$ ions such as by contact with an aqueous solution of strong inorganic acid such as hydrochloric acid or with an aqueous solution containing ammonium ions, followed by drying the product and calcination at a temperature in excess of 350° C. for one hour or more. The product may then be activated prior to contact with the feedstock by heating as described above.

The silica containing catalysts of this invention may be employed as such or may be combined with a binder or support material such an inorganic oxide or clay binder. Non-limiting examples of such binder materials include alumina, zirconia, silica, magnesia, thoria, titania, boria and combinations thereof, generally in the form of dried oxide gels and/or gelatinous precipitates. Suitable clay materials include, by way of example, montmorillonite, kaolinite, talc, pyrophyilite and the like. The relative proportion of silicon-containing catalyst to total composition of catalyst and binder may vary widely, with the preferred level of catalyst content being from about 50 to about 95% by weight, most preferably from about 70 to 90% by weight.

The catalyst is most effectively used in various fabricated forms of spheres, granules and pellets having a diameter of from about 1/32 to ¼ inch.

The reactors employed in the cracking process described in the following Examples are pilot plant micro reactors equipped with a fixed bed and preferably operated in the up flow mode.

One reactor is a 1.9 cm internal diameter reactor designed to operate at up to 500° C. and at relatively higher space velocities, i.e., above about 2 wt/wt/hour. The other reactor is a 2.4 cm internal diameter reactor also designed to operate at up to 500° C., but at lower space velocities. Catalyst loading of pellets in the reactors is in the order of about 100 cc in volume.

The process is also applicable for use in commercial scale reactors as well. These include reformer type reactors having a cyclic fixed bed system; salt bath reactors adapted to accommodate both endothermic reactor duty and the higher temperatures required for catalyst regeneration; continuous, suspension catalytic reactor systems where the feedstack is pumped with a small amount of catalyst directly through heater coils and the product is separated in a flash unit; and moving bed reactors. The reactors may thus be of the fixed or fluid bed modes and be equipped for intermittent or continuous catalyst regeneration.

The process of this invention is carried out such that the conversation of $C_{10}{}^+$ olefin feedstock to $C_9$ and lower olefins is carried out in the vapor phase by contact in the catalyst bed reaction zone under effective conversion conditions. These conditions generally include a temperature within the range of from about 250° C. up to about 450° C., pressures from atmospheric up to about 300 psig and a space velocity within the range of from about 0.5 up to about 4 wt/wt/hour.

Specific process conditions will differ depending upon the identity of the cracking catalyst and the selectivity of that catalyst under various process conditions towards the production of $C_6$ to $C_9$ olefins, the effect of process conditions on catalyst life and the amount of build up of catalyst poisons such as coke. For example, at operating pressures in excess of about 300 psig there is an unacceptable coke buildup on the surface of the catalyst which leads to relatively fast catalyst deactivation.

Coke buildup is caused by the deposition of carbonaceous materials on the catalyst surface and pores as a consequence of complex side reactions accompanying the cracking reaction, such as aromatization, polymerization, alkylation and the like. The deposition of coke tends to seriously impair the catalytic efficiency of the catalyst for the principal reaction and the conversion reaction is thereafter suspended or greatly diminished in efficiency after coke to the extent of 5-10% by weight has accumulated on the catalyst. This then requires regeneration of the catalyst by burning off the coke at temperatures ranging from 400° to 550° C., followed by reintroduction of the catalyst into the reconversion stage of the cycle.

Accordingly, preferred cracking pressures are less than 300 psig, with the preferred range being from about 50 to about 100 psig. The most preferred cracking pressure is 75 psig.

A particular advantage of the process of this invention is that it may be conducted at relatively low cracking temperatures within the range of from about 250° C. up to about 450° C. while still obtaining good conversions to $C_9$ and lower olefins and excellent selectivity towards the production of olefins in the $C_6$ to $C_9$ hydrocarbon fraction boiling within the 20° to 154° C. range. The process generally yields olefin selectivity in the $C_6$ to $C_9$ hydrocarbon fraction boiling within the 20° to 154° C. range of from about 70 to 100 volume percent and conversion of $C_{10}{}^+$ olefin feedstock to $C_9$ and lower olefins of from about 20 to about 70 weight percent, depending on the identity of the catalyst and process conditions. Of the amount of $C_{10}$ and higher olefins converted to $C_9$ and lower olefins the process provides a net yield gain in the cracked product (the gain after subtracting the quantity of $C_6$ to $C_9$ olefins originally present in the feedstock) of at least about 5% by weight, and more generally in the range of from about 10 to about 30% by weight. Generally speaking, the feedstock contains less than about 70% by volume of olefins in the $C_6$ to $C_9$ hydrocarbon fraction boiling within the range of 20° to 154° C. prior to cracking.

Of particular advantage is the fact that the present process may be conducted at cracking temperatures of less than about 400° C., for example from about 275° C. to less than about 400° C., while obtaining excellent and unexpected conversion rates to $C_9$ and lower olefins and high olefinic selectively content in the $C_6$ to $C_9$ hydrocarbon fraction boiling in the 20° to 154° C. range. Operation at temperatures below about 400° C. offers the distinct advantage of diminished coke buildup, process economy, and further selectivity toward $C_6$ to $C_9$ olefin production at the expense of $C_3$ and $C_4$ olefin production.

The process is generally conducted at a space velocity within the range of from about 0.5 up to about 4 wt/wt/hour. Space velocity is defined as the weight of feedstock passing through a given weight of catalyst per hour. It has been found that the process is selective towards the production of larger quantities of $C_6$ to $C_9$ olefins and lesser quantities of $C_3$ and $C_4$ olefins at these relatively low space velocities. Best results on a small scale are achieved by conducting the process at a space velocity of about 1 wt/wt/hour.

Feedstocks which may be processed in accordance with this invention contain a major proportion of branched $C_{10}$ and higher olefins, more particularly at least about 70 weight percent of $C_{10}$ and high olefins. A typical feedstock composition contains at least about 70 weight percent of branched $C_{10}$ and $C_{11}$ olefins combined, up to about 15 weight percent of branched $C_9$ olefins and up to about 20 weight percent of branched $C_{12}$ and higher olefins. The composition of a typical feedstock which may be processed in accordance with this invention is as follows:

| | |
|---|---|
| $C_8$ | 0.1 weight % |
| $C_9$ | 3.4 weight % |
| $C_{10}$ | 21.7 weight % |
| $C_{11}$ | 72.7 weight % |
| $C_{12}$ | 2.1 weight % |
| Total | 100.0 weight % |

The feedstocks may further be characterized as water white in color and containing at least about 95 volume % of branched olefins (predominantly single and double branches) and having a density within the range of from about 0.75 to 0.79 kg/l at 15° C., a Bromine Number of from about 110 to 130, and a sulphur content of less than about 20 ppm.

The cracked product produced in accordance with the process of this invention has been found to be considerably less branchy and more linear in nature than the precursor feedstock and contains very low overall levels of saturated hydrocarbons, generally less than 10 volume percent. Thus the cracked product is highly olefinic, contains an enhanced content of $C_6$ to $C_9$ olefins and a very high olefinic content in the $C_6$ to $C_9$ hydrocarbon fraction boiling in the 20° to 154° C. range, generally at least about 70 volume percent olefins and frequently from about 85 to 100 volume percent olefins, depending on the catalyst and processing conditions employed.

The $C_6$ to $C_9$ olefin materials may subsequently be separated from the cracked product by standard techniques known in the art such as vapor separation, distillation and fractional distillation.

Samples of total product were taken in evacuated sampling cylinders downstream of the reactor, but upstream of the product separator. Composite liquid product samples were taken downstream of the product separator. The samples of all products were analyzed by Capillary Column Gas Chromatograph, which gives a complete carbon number distribution of products from $C_2$ to $C_{14+}$, including the $C_3$ and $C_4$ isomer split.

The carbon number distribution of the liquid product phases was analyzed by non-selective capillary column hydrogenation gas chromatograph, which identified the isomers in the $C_6$ to $C_9$ carbon number range. The olefin content of the liquid product phases was determined by Fluorescence Indicator Absorption techniques (FIA).

The following examples are illustrative of the invention.

EXAMPLE 1

A mixture of branched Higher Olefins with the following properties was taken as the feed to the reactor:

| | |
|---|---|
| Olefins (vol. %) | 98.4 |
| Density (kg/L at 15° C.) | 0.764 |
| Branchiness | 1.76 |
| Sulphur (ppm) | 3 |
| Carbon Number Distribution | Wt. % |
| $C_8$ | 0.1 |
| $C_9$ | 3.4 |
| $C_{10}$ | 21.7 |
| $C_{11}$ | 72.7 |
| $C_{12}$ | 2.1 |

The reactor was packed with extrudates of activated precipitated silica (Silica NOI from United Catalysts Inc.) as received from the manufacturer and having the following characteristics:

| | |
|---|---|
| Surface Area (M²/g): | 179.1 |
| Pore Volume (cc/g): | 1.364 |
| Composition: | >99% $SiO_2$ |
| Size: | ¼" Extrudates |
| Chlorides, %: | 1.6 |
| TBA Adsorption, moles/g: | $6.63 \times 10^{-4}$ |
| TBA Desorption, moles/g: | $6.16 \times 10^{-4}$ |

The catalyst was heat activated in the reactor for one hour at 400° C. The feed was passed over the catalyst in a continuous mode at reactor conditions shown in Table 1 which also depicts the carbon number distribution of the product.

TABLE 1

| CONDITIONS | | | | | |
|---|---|---|---|---|---|
| Catalyst | Untreated PPT. Silica Extrudate | | | | |
| Temperature, °C. | 350 | | 350 | 400 | 400 |
| Pressure, PSIG | ---------- 75 ---------- | | | | |
| Space Velocity, WT/WT/h | 4.0 | | 1.0 | 4.0 | 1.0 |
| Cat. Hrs | 2.0 | | 52.0 | 74.0 | 124.0 |
| Product Carbon No. Distribution, wt. % | | | | | |
| $C_3$ and lighter | 0.0 | | 0.0 | 0.1 | 0.3 |
| $C_4$ | 0.0 | | 0.0 | 0.1 | 0.4 |
| $C_5$ | 0.0 | | 0.0 | 0.1 | 0.2 |
| $C_6$ | 0.0 | | 0.0 | 0.2 | 0.4 |
| $C_7$ | | Feed | 0.1 | 0.0 | 0.1 | 0.4 |
| $C_8$ | $C_8$ | 0.1 | 0.1 | 0.1 | 0.2 | 0.4 |
| $C_9$ | $C_9$ | 3.4 | 5.9 | 5.8 | 6.2 | 6.0 |
| $C_{10}$ | $C_{10}$ | 21.7 | 33.1 | 32.9 | 33.4 | 32.2 |
| $C_{11}$ | $C_{11}$ | 72.7 | 57.8 | 58.2 | 56.8 | 56.5 |
| $C_{12}$ | $C_{12}$ | 2.1 | 3.0 | 3.0 | 2.8 | 3.2 |
| $C_{13}$ | | | 0.0 | 0.0 | 0.0 | 0.0 |
| $C_{14+}$ | | | 0.0 | 0.0 | 0.0 | 0.0 |
| Conversion to $C_9$ and Lighter, wt. %* | | | 2.6 | 2.5 | 3.5 | 4.6 |
| Yield of $C_7$ to $C_9$, wt. %* | | | 2.6 | 2.5 | 3.0 | 3.3 |
| Olefins in 20°-154° C. Fraction, LV % | ---------- >96 ---------- | | | | |

*$C_8$ and $C_9$ molecules in feed subtracted from product.

EXAMPLE 2

A mixture of higher olefins taken from the same lot used in Example 1 was passed over a sample of precipitated silica catalyst prepared by the following procedure:

100 g of the catalyst of Example 1 was washed with an aqueous solution containing 10% $NH_4Cl$. The catalyst was air dried under vacuum at 100° C., calcined at 500° C. in a muffle furnace, charged into a fixed bed reactor and heat activated for one hour at 400° C. The reaction conditions and reaction products are shown in Table 2.

This example illustrates the finding that precipitated silica activated with $NH_4Cl$ is a very effective catalyst to crack higher olefins. Thus, not only the conversion per pass is significantly increased, but the product is highly olefinic with most of these olefins being in the $C_6$ to $C_9$ carbon range.

TABLE 2

Cracking of Higher Olefins

| CONDITIONS | | | | | |
|---|---|---|---|---|---|
| Catalyst | | | Ammonium Chloride Treated PPT Silica | | |
| Temperature, °C. | | | 400 | 400 | 400 |
| Pressure, psig | | | 75 | 300 | 100 |
| Space Velocity, wt/wt/h | | | 1.0 | 1.0 | 0.5 |
| Catalyst Life, USG Product/lb. | ---------- 1.0 ---------- | | | | |
| Product Carbon No. Distribution, wt. % | | | | | |
| $C_4$ and Lighter | | | 9.1 | 9.4 | 11.4 |
| $C_5$ | | | 2.1 | 3.5 | 3.3 |
| $C_6$ | | | 10.9 | 8.7 | 14.5 |
| $C_7$ | | Feed | 7.4 | 6.4 | 9.1 |
| $C_8$ | $C_8$ | 0.1 | 4.9 | 4.7 | 5.8 |
| $C_9$ | $C_9$ | 3.4 | 7.4 | 7.9 | 6.8 |
| $C_{10}$ | $C_{10}$ | 21.7 | 11.9 | 13.4 | 8.8 |
| $C_{11}$ | $C_{11}$ | 72.7 | 32.2 | 31.4 | 24.2 |
| $C_{12}$ | $C_{12}$ | 2.1 | 11.7 | 12.1 | 10.9 |
| $C_{13}$ | | | 1.0 | 1.3 | 2.2 |
| $C_{14+}$ | | | 1.4 | 1.2 | 3.0 |
| Conversion to $C_9$ & Lighter, wt. %* | | | 38.3 | 36.6 | 47.4 |
| Yield $C_7$ to $C_9$, wt. %* | | | 16.2 | 15.0 | 18.2 |
| Olefins in 20-154° C. Fraction, LV % | | | 96.0 | 82.8 | 95.2 |

*$C_8$ and $C_9$ molecules in feed subtrated from product.

The amount of coke formed on the catalyst in 72 hours was 32 wt. %.

EXAMPLE 3

In this example, a sample of the mixture of higher olefins described in Example 1 was made to react over a bed of crystalline hydrogen ZSM-5 extrudates (ZEO-CHEM) obtained from United Catalysts Inc. The catalyst in the form of 1/16" pellets was packed as is, without prior treatment, into the reactor.

This sample of zeolite had the following properties:

| | |
|---|---|
| Surface Area | 359 mg/g |
| Pore Volume | 0.54 cc/g |
| Median Pore Diameter | 250 Angstrom |
| Crush Strength | 2.08 lbs./MM |
| Bulk Density | 38 lbs./ft$^3$ |
| SiO$_2$/Al$_2$O$_3$ Ratio | 70:1 |
| Strong Acidity | 0.87 mg. NH$_3$/100 mg. |
| Weak Acidity | 0.26 mg. NH$_3$/100 mg. |

The operating conditions and the distribution of products are as shown in Table 3.

This data clearly indicate that untreated ZSM-5 has substantial catalytic cracking activity and good selectivity toward the production of C$_7$ to C$_9$ olefins.

TABLE 3

| CONDITIONS | | | | |
|---|---|---|---|---|
| Catalyst | | Untreated ZSM-5 Extrudates | | |
| Temperature, °C. | | 275 | 300 | 325 |
| Pressure, PSIG | | ---------- 75 ---------- | | |
| Space Velocity, WT/WT/h | | ---------- 1.0 ---------- | | |
| Cat. Life USG Product/lb. | | 0.4 | 2.6 | 4.2 |
| Cat. Hrs. | | 6.0 | 30.0 | 54.0 |
| Product Carbon No. Distribution, wt. % | | | | |
| C$_4$ and Lighter | | 6.3 | 13.8 | 6.5 |
| C$_5$ | | 3.3 | 7.4 | 3.5 |
| C$_6$ | | 12.8 | 17.0 | 12.7 |
| C$_7$ | Feed | 7.9 | 9.3 | 8.7 |
| C$_8$ | C$_8$ 0.1 | 5.3 | 7.5 | 7.2 |
| C$_9$ | C$_9$ 3.4 | 6.7 | 9.3 | 9.3 |
| C$_{10}$ | C$_{10}$ 21.7 | 14.6 | 11.7 | 15.0 |
| C$_{11}$ | C$_{11}$ 72.7 | 30.4 | 17.7 | 26.3 |
| C$_{12}$ | C$_{12}$ 2.1 | 6.5 | 5.4 | 7.8 |
| C$_{13}$ | | 2.7 | 0.9 | 1.9 |
| C$_{14}$+ | | 3.5 | 0.0 | 1.1 |
| Conversion to C$_9$ and Lighter, wt. %* | | 38.8 | 60.8 | 44.4 |
| Yield of C$_7$ to C$_9$, wt. %* | | 16.4 | 22.6 | 21.7 |
| Olefins in 20°-154° C. Fraction, LV % | | ---------- 86.4 ---------- | | |

*C$_8$ and C$_9$ molecules in feed subtracted from product.

Coke deposited on the catalyst was 3.8 wt % after 72 hrs.

EXAMPLE 4

This example illustrates the use of ZSM-5 treated with monoammonium phosphate in cracking higher olefins of the feed used in Example 1. This catalyst of modified acidity is prepared by mixing 100 g. of ZSM-5 catalyst with a 2% mono-ammonium phosphate solution at room temperature for 2 hours. The catalyst is then separated by filtration from the solution, washed with 2 equal portions of distilled water and dried under vacuum at 100° C. for 4 hours. The catalyst is then calcined for 1 hour at 500° C. in a muffler furnace.

The catalyst is then heat activated at 400° C. for one hour in the reactor prior to pumping the feed into the reactor.

The reactor conditions and the product distribution are given in Table 4.

TABLE 3

| CONDITIONS | | |
|---|---|---|
| Catalyst | | Phosphate Treated ZSM-5 Extrudates |
| Temperature, °C. | 275 | 325 |
| Pressure, PSIG | ------ 75 ------ | |
| Space Velocity, WT/WT/h | ------ 1.0 ------ | |
| Cat. Life USG Product/lb. | ------ 1.0 ------ | |
| Product Carbon No. Distribution wt. % | | |
| C$_4$ and Lighter | 6.4 | 9.3 |
| C$_5$ | 2.8 | 3.8 |
| C$_6$ | 12.7 | 18.2 |
| C$_7$ Feed | 7.3 | 9.8 |
| C$_8$ C$_8$ 0.1 | 4.6 | 7.0 |
| C$_9$ C$_9$ 3.4 | 6.0 | 7.9 |
| C$_{10}$ C$_{10}$ 21.7 | 14.7 | 11.8 |
| C$_{11}$ C$_{11}$ 72.7 | 32.1 | 23.6 |
| C$_{12}$ C$_{12}$ 2.1 | 7.3 | 5.9 |
| C$_{13}$ | 2.6 | 1.6 |
| C$_{14}$+ | 3.5 | 1.1 |
| Conversion to C$_9$ and Lighter, wt. %* | 36.3 | 52.5 |
| Yield of C$_7$ to C$_9$, wt. %* | 14.4 | 21.2 |
| Olefins in 20°-154° C. Fraction, LV % | 84.0 | 86.7 |

*C$_8$ and C$_9$ molecules in feed subtracted from product.

Coke deposited on the catalyst was 3.8 wt % after 72 hrs.

EXAMPLE 5

In this example, the feed of Example 1 is passed over an untreated sample of silicalite (SP115 from Union Carbide Co.). This zeolite catalyst has a composition of >99% SiO$_2$ and a pore volume of 0.19 cc/g. The catalyst was first heat activated for one hour at 400° C. in the reactor.

The operating conditions and the product distribution are shown in Table 5. As can be seen from the data of Table 5, untreated silicalite does not exhibit quite as high an activity for the cracking of olefins as ZSM-5.

TABLE 5

| CONDITIONS | | | | |
|---|---|---|---|---|
| Catalyst | | Untreated Silicalite | | |
| Temperature, °C. | | 300 | 355 | 400 |
| Pressure, PSIG | | ---------- 75 ---------- | | |
| Space Velocity, WT/WT/h | | ---------- 1.0 ---------- | | |
| Cat. Life USG Product/lb. | | 0.1 | 0.4 | 1.5 |
| Cat. Hrs. | | 6.0 | 30.0 | 54.0 |
| Product Carbon No. Distribution, wt. % | | | | |
| C$_4$ and Lighter | | 0.4 | 2.0 | 10.4 |
| C$_5$ | | 0.1 | 0.6 | 2.4 |
| C$_6$ | | 0.7 | 4.4 | 11.6 |
| C$_7$ | Feed | 0.4 | 2.2 | 4.7 |
| C$_8$ | C$_8$ 0.1 | 0.3 | 1.0 | 1.9 |
| C$_9$ | C$_9$ 3.4 | 3.2 | 3.3 | 2.4 |
| C$_{10}$ | C$_{10}$ 21.7 | 23.8 | 21.2 | 14.5 |
| C$_{11}$ | C$_{11}$ 72.7 | 67.0 | 60.0 | 44.4 |
| C$_{12}$ | C$_{12}$ 2.1 | 3.8 | 3.7 | 6.7 |
| C$_{13}$ | | 0.3 | 0.7 | 1.0 |
| C$_{14}$+ | | 0.0 | 0.0 | 0.0 |
| Conversion to C$_9$ and Lighter, wt. %* | | 1.6 | 10.9 | 29.9 |
| Yield of C$_7$ to C$_9$, wt. %* | | 0.4 | 3.0 | 5.5 |
| Olefins in 20°-154° C. Fraction, LV % | | ---------- 100 ---------- | | |

*C$_8$ and C$_9$ molecules in feed subtracted from product.
Coke deposited on the catalyst was 9.7 wt % after 72 hrs.

EXAMPLE 6

This example is provided to show the desirable effect of pretreatment with monoammonium phosphate on the cracking activity of Silicalite. The pretreatment consisted of the following procedure:

A 100 g sample of the silicalite of Example 5 in the form of extrudates was mixed with a 2% Monoammonium phosphate solution at ambient temperature for 2 hours. The catalyst was then separated by filtration and washed with two equal portions of distilled water. The catalyst was dried under vacuum at 100° C. for 4 hours then calcined for 1 hour at 500° C. in a muffle furnace. The catalyst was then heat activated for one hour at 400° C. in the reactor.

The operating conditions and product distribution are given in Table 6.

As can be seen from the data of Table 6, the treatment of the catalyst to produce the acid form increases the percent per pass conversion and increases the $C_6$ to $C_9$ fraction at the expense of some reduction in the percentage of olefins in the cracked product and increasing amounts of $C_4$ and lighter fractions.

TABLE 6

| CONDITIONS | | | |
|---|---|---|---|
| Catalyst | | | Monoammonium Phosphate Treated Silicalite |
| Temperature, °C. | | | ———350——— |
| Pressure, PSIG | | | ———750——— |
| Space Velocity, Product/lb. | | | ———1.0——— |
| Cat. Life USG Product/lb. | | | 1.0——— |
| Product Carbon No. Distribution | | | |
| $C_4$ + Lighter | | | 13.5 |
| $C_5$ | | | 5.6 |
| $C_6$ | | | 12.9 |
| $C_7$ | | Feed | 6.4 |
| $C_8$ | $C_8$ | 0.1 | 5.0 |
| $C_9$ | $C_9$ | 3.4 | 6.6 |
| $C_{10}$ | $C_{10}$ | 21.7 | 13.2 |
| $C_{11}$ | $C_{11}$ | 72.7 | 32.2 |
| $C_{12}$ | $C_{12}$ | 2.1 | 4.0 |
| $C_{13}$ | | | 0.3 |
| $C_{14}+$ | | | 0.3 |
| Conversion to $C_9$ and Lighter, wt. %* | | | 46.5 |
| Yield of $C_7$ to $C_9$, wt. %* | | | 14.5 |
| Olefins in 20°-154° C. Fraction, LV % | | | 73.4 |

*$C_8$ and $C_9$ molecules in feed subtracted from product.
Coke deposited on the catalyst was 9.7 wt. % after 72 hrs.

EXAMPLE 7

This example illustrates the use of Beta zeolite (Valfor C-815 from P. Q. Inc.) for the cracking of $C_9+$ olefins. This zeolite is in the crystal form and had a silica/aluminum ratio of 12. It was mixed with 20% by weight kaolin and extruded into 3/16 inch extrudates.

The extrudates were loaded into a fixed bed reactor and heat activated at 400° C. for one hour. The reactor conditions and the product distribution are shown in Table 7.

These data indicate that Zeolite Beta has good activity and desirable selectivity for $C_7$ to $C_9$ olefins without the formation of excessive amounts of $C_4$ and lighter products.

TABLE 7

| CONDITIONS | | | | |
|---|---|---|---|---|
| Catalyst | | | Beta Zeolite | |
| Temperature, °C. | | | ———300——— | |
| Pressure, PSIG | | | ———75——— | |
| Space Velocity, WT/WT/h | | | ———1.0——— | |
| Cat. Life USG Product/lb. | | | 0.5 | 2.4 |
| Product Carbon No. Distribution wt. % | | | | |
| $C_4$ + Lighter | | | 10.3 | 5.0 |

TABLE 7-continued

| | | | | |
|---|---|---|---|---|
| $C_5$ | | | 8.1 | 2.4 |
| $C_6$ | | | 14.1 | 10.2 |
| $C_7$ | | Feed | 10.8 | 7.0 |
| $C_8$ | $C_8$ | 0.1 | 6.9 | 3.5 |
| $C_9$ | $C_9$ | 3.4 | 8.4 | 5.9 |
| $C_{10}$ | $C_{10}$ | 21.7 | 12.7 | 15.9 |
| $C_{11}$ | $C_{11}$ | 72.7 | 19.3 | 36.9 |
| $C_{12}$ | $C_{12}$ | 2.1 | 6.6 | 9.0 |
| $C_{13}$ | | | 1.4 | 1.8 |
| $C_{14}+$ | | | 1.4 | 2.4 |
| Conversion to $C_9$ and Lighter, wt. %* | | | 55.1 | 30.5 |
| Yield of $C_7$ to $C_9$, wt. %* | | | 22.6 | 12.9 |
| Olefins in 20°-154° C. Fraction, LV % | | | | 87.4 |

*$C_8$ and $C_9$ molecules in feed subtracted from product.

EXAMPLE 8

This example illustrates the use of a magnesium exchanged version of the Beta Zeolite catalyst used in Example 7. This catalyst was prepared by exchanging Beta Zeolite with magnesium. A solution containing 10 g of Beta Zeolite, 17 g. of magnesium nitrate and 80 g. of deionized water (DW) was heated at 85° C. for 2 hours with constant stirring. This slurry was then vacuum filtered and washed with 300 g. DW on the filter. The filter cake was dried for 1 hour at 150° C. followed by 1 hour at 350° C. the dried filter cake was then returned to an identical exchange solution described above and exchanged a second time. The filter cake was washed on the filter with 500 g. DW, then dried at 150° C. The dried Mg-Beta Zeolite was then mixed with 20% by weight kaolin, moistened into a paste, extruded into 3/16 inch pellets, and the extrudates dried in an air oven.

The resulting catalyst had a silica/aluminum ratio of 12, a pore volume of 0.78 cc/g. and a surface area of 110 $m^2/g$.

This catalyst was placed in a fixed bed reactor and calcined for 1 hour at 400° C. The olefinic hydrocarbon mixture described in Example 1 was passed over this catalyst in continuous mode. The reaction conditions and the product distribution are shown in Table 8.

These data show that the cation exchanged zeolite Beta performs similarly to ZSM-5 with respect to overall activity and exhibits a substantial increase in olefin selectivity as compared with ZSM-5.

TABLE 8

| CONDITIONS | | | | |
|---|---|---|---|---|
| Catalyst | | | $Mg^{++}$ Beta Zeolite (20% Kaolin) | |
| Temperature, °C. | | | ———300——— | |
| Pressure, PSIG | | | ———75——— | |
| Space Velocity, WT/WT/h | | | ———1.0——— | |
| Cat. Life USG Product/lb. | | | 0.5 | 1.6 |
| Product Carbon No. Distribution | | | | |
| $C_4$ + Lighter | | | 12.9 | 5.8 |
| $C_5$ | | | 8.7 | 2.6 |
| $C_6$ | | | 14.1 | 10.4 |
| $C_7$ | | Feed | 11.4 | 5.9 |
| $C_8$ | $C_8$ | 0.1 | 6.6 | 2.5 |
| $C_9$ | $C_9$ | 3.4 | 8.4 | 4.8 |
| $C_{10}$ | $C_{10}$ | 21.7 | 13.4 | 18.2 |
| $C_{11}$ | $C_{11}$ | 72.7 | 16.0 | 39.9 |
| $C_{12}$ | $C_{12}$ | 2.1 | 3.4 | 7.1 |
| $C_{13}$ | | | 1.4 | 1.2 |
| $C_{14}+$ | | | 3.1 | 1.6 |
| Conversion to $C_9$ and Lighter, wt. %* | | | 59.2 | 28.5 |

TABLE 8-continued

| | | |
|---|---|---|
| Yield of $C_7$ to $C_9$, wt. %* | 22.9 | 9.7 |
| Olefins in 20°–154° C. Fraction, LV % | ----- 92.5 ----- | |

*$C_8$ and $C_9$ molecules in feed substracted from product.

The following Examples 9–11 illustrate the use of hydrogen mordenite and modified versions thereof in the cracking of a mixture of higher $C_{10}/C_{11}$ branched olefins having the following composition:

| | |
|---|---|
| $C_8$ | 0.1 wt. % |
| $C_9$ | 3.4 wt. % |
| $C_{10}$ and heavier | 96.5 wt. % |

EXAMPLE 9

A commercial sample of hydrogen mordenite, having an Si/Al ratio of 10 and crystal sizes less than 0.2 microns (Laporte HM-2), was exchanged in a manner identical to that described in previous Example 8 for zeolite beta, formed into 3/16 inch extrudates and tested in the mode described in Example 8. The results, shown in Table 9, show that this material has very good activity and selectivity for the desirable $C_7$ to $C_9$ fraction, with moderate olefin selectivity.

EXAMPLE 10

A 30 gm. sample of the hydrogen mordenite used in Example 9 (Laporte HM-2) was first refluxed with 300 mls. 3N HCl solution for 4 hours. It was then vacuum filtered, washed with 300 mls. dilute HCl solution (pH=2), followed by 500 mls. DI water. This dealuminated, acid modified mordenite, was then magnesium exchanged with 30 gm. $Mg(NO_3)_2 \cdot 6H_2O$ dissolved in 300 mls. $H_2O$ at 60° C. for one hour; filtered on a vacuum filter; and washed with 600 mls. of deionized water (DW). The filter cake was returned to the beaker and reexchanged in an identical manner, followed by filtration and washing with 1500 mls. DW. This final material was mixed with 20% wt. kaolin and extruded into 3/16 inch extrudates, dried, and evaluated in the manner described in Example 8. The catalytic data of Table 9 shows that this lower acidity mordenite retains excellent activity and $C_7$ to $C_9$ selectivity while showing marked improvement in olefin selectivity.

EXAMPLE 11

A second sample of commercial mordenite having an Si/Al ratio of 10.5 and crystal sizes in the 0.2 micron range (Conteka CBV-20A) was exchanged in a manner described in Example 10, similarly made into 3/16 inch extrudates, and catalytically tested in the cracking of $C_{13+}$ olefins. The results, shown in Table 9 further illustrate the desirable activity and selectivity characteristics of small crystal (<0.5 microns), high silica, mordenites for selective higher olefin cracking.

TABLE 9

| CATALYST | EX. 9 | | EX. 10 | | EX. 11 | |
|---|---|---|---|---|---|---|
| CONDITIONS | | | | | | |
| Temperature, °C. | ------------- 300 ------------- | | | | | |
| Pressure, PSIG | ------------- 75 ------------- | | | | | |
| Space Velocity, WT/WT/h | ------------- 1.0 ------------- | | | | | |
| Sampling Time, Cat hrs | 3 5 | | 3 7 | | 3 5 7 | |
| Product Carbon No. Distribution, wt. % | | | | | | |
| $C_5$ + Lighter | 15.7 | 10.4 | 12.5 | 5.7 | 13.7 | 10.6 3.5 |
| $C_6$ | 9.8 | 7.6 | 13.7 | 8.5 | 11.6 | 9.7 4.1 |
| $C_7$ Feed 12.6 | 10.2 | 15.8 | 11.4 | 11.9 | 12.4 | 8.1 |
| $C_8$ 0.1 | 18.0 | 12.2 | 13.6 | 9.8 | 8.3 | 9.1 6.4 |
| $C_9$ 3.4 | 24.8 | 16.9 | 13.8 | 10.1 | 8.5 | 10.5 8.5 |
| $C_{10}$ and heavier 96.5 | 19.1 | 42.6 | 30.6 | 45.5 | 46.0 | 47.7 69.4 |
| Conversion to $C_9$ and Lighter, Wt %* | 77.4 | 53.0 | 65.9 | 42.0 | 50.5 | 48.8 27.1 |
| Yield of $C_7$ to $C_9$, wt. %* | 51.9 | 35.0 | 39.7 | 27.8 | 25.2 | 28.5 19.5 |
| Olefins (20–154° C.) Frac, Vol. % | -- 41.2 -- | | -- 81.1 -- | | ---- 57.7 ---- | |

What we claim is:

1. A process for converting an olefin feedstock containing at least about 50% by weight of $C_{10}$ and higher olefins into a product containing $C_9$ and lower olefins with an olefin selectivity in the $C_6$ to $C_9$ range of about 70 to 100 volume percent comprising contacting said olefin feedstock under cracking conditions at a temperature of 275° C. to less than 400° C. and a space velocity of 0.5 to 4 wt/wt/hour and a pressure of from about atmospheric up to about 300 psig with a catalyst material selected from the group consisting of crystalline aluminosilicates and silicas, amorphous precipitated silica and ion exchanged or acid forms thereof.

2. The process of claim 1 wherein said feedstock contains at least about 70% by weight of $C_{10}$ and higher olefins.

3. The process of claim 1 wherein said pressure is within the range of from about 50 up to about 100 psig.

4. The process of claim 1 wherein said catalyst is a crystalline aluminosilicate compound having the formula:

$$0.9 \pm 0.3 M_{2/n}O:Al_2O_3:5-300SiO_2:zH_2O$$

wherein M is a cation or mixture of cations, n is the valence or average valence of said cation(s) and z ranges from 0 to about 40.

5. The process of claim 4 wherein M is an ion is selected from the group consisting of alkali metal, alkaline earth metal, hydrogen, ammonium, and mixtures thereof.

6. The process of claim 5 wherein M is alkali metal and said catalyst is modified by ion exchange wherein a portion or all of said alkali metal ion is replaced with an ion selected from the group consisting of ammonium, hydrogen and a metal ion selected from Groups II to VIII of the Periodic Table.

7. The process of claim 6 wherein said replacing ion is ammonium.

8. The process of claim 2 wherein said catalyst is zeolite ZSM-5 or siliceous derivatives thereof.

9. The process of claim 8 wherein said catalyst is prepared by ion exchange with an ammonium compound and subsequent calcination.

10. The process of claim 9 wherein said ammonium compound is ammonium phosphate.

11. The process of claim 1 wherein said catalyst is amorphous precipitated silica having an $SiO_2$ content of greater than 99% by weight.

12. The process of claim 11 wherein said amorphous precipitated silica is modified under ion exchange conditions to introduce ammonium ions into the silica, followed by calcination.

13. The process of claim 1 wherein said catalyst is zeolite-beta.

14. The process of claim 13 wherein said zeolite-beta is modified by ion exchange with magnesium or calcium, followed by calcination.

15. The process of claim 2 wherein the catalyst is a mordenite.

16. The process of claim 15 wherein said mordenite is ion exchanged with magnesium or calcium, followed by calcination.

17. The process of claim 15 wherein said mordenite has a Si to Al ratio in the range of from about 5 to 1 to about 15 to 1.

18. The process of claim 15 wherein said mordenite has a crystal size of less than about 0.5 micron.

* * * * *